(12) United States Patent
Favuzzi et al.

(10) Patent No.: US 7,758,809 B2
(45) Date of Patent: *Jul. 20, 2010

(54) METHOD AND SYSTEM FOR PRETREATMENT OF TISSUE SLIDES

(75) Inventors: John Favuzzi, Santa Barbara, CA (US); Benno Guggenheimer, Fort Collins, CO (US); Jeff Rau, Fort Collins, CO (US); Marc Key, Ojai, CA (US); Robert Lathrop, San Jose, CA (US); Rosanne Welcher, Ventura, CA (US)

(73) Assignee: Dako Cytomation Denmark A/S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/630,665

(22) Filed: Dec. 3, 2009

(65) Prior Publication Data

US 2010/0081167 A1    Apr. 1, 2010

Related U.S. Application Data

(63) Continuation of application No. 10/731,316, filed on Dec. 8, 2003, now Pat. No. 7,648,678.

(60) Provisional application No. 60/435,601, filed on Dec. 20, 2002.

(51) Int. Cl.
*G01N 1/28* (2006.01)
*G01N 1/30* (2006.01)

(52) U.S. Cl. .............................. 422/63; 422/65; 436/43; 436/47; 436/49; 436/174; 435/40.5; 435/287.1; 435/287.3; 435/288.3

(58) Field of Classification Search ....................... None
See application file for complete search history.

(56) References Cited

U.S. PATENT DOCUMENTS 3,219,416 A    11/1965    Natelson (Continued)

FOREIGN PATENT DOCUMENTS

AT    0178812 E    4/1999

(Continued)

OTHER PUBLICATIONS

European Patent Application No. 91 90 8695 Supplementary European Search Report, Search completed Mar. 26, 1993.

(Continued)

*Primary Examiner*—P. Kathryn Wright
(74) *Attorney, Agent, or Firm*—Finnegan, Henderson, Farabow, Garrett & Dunner, L.L.P.

(57) ABSTRACT

The present invention concerns a method and an apparatus for automatic staining of at least one tissue sample accommodated on a slide by applying reagents. The system may include at least one slide provided in a slide rack, a fluid containment element, a slide holder, a vertical slide positioner to pivot the slides to a vertical position, and a slide immerser element to immerse the vertical slide into a fluid containment element or even a dip tank. By pivoting the slides from a horizontal to a vertical position, an automated method and apparatus for carrying out a pretreatment in an automated staining apparatus may be provided. The pivoting of slides may ensure an appropriate orientation of the slides for both the pretreatment and the staining processes.

20 Claims, 8 Drawing Sheets

U.S. PATENT DOCUMENTS

| | | |
|---|---|---|
| 3,398,935 A | 8/1968 | Livesey et al. |
| 3,482,082 A | 12/1969 | Isreeli |
| 3,513,320 A | 5/1970 | Weldon |
| 3,553,438 A | 1/1971 | Blitz et al. |
| 3,574,064 A | 4/1971 | Binnings at al. |
| 3,592,605 A | 7/1971 | Noma et al. |
| 3,600,900 A | 8/1971 | Buddecke |
| 3,644,715 A | 2/1972 | Holderith |
| 3,660,638 A | 5/1972 | Oberli |
| 3,680,967 A | 8/1972 | Englehardt |
| 3,772,154 A | 11/1973 | Isenberg et al. |
| 3,801,775 A | 4/1974 | Acker |
| 3,807,851 A | 4/1974 | Knox et al. |
| 3,831,006 A | 8/1974 | Chaffin, III et al. |
| 3,851,972 A | 12/1974 | Smith et al. |
| 3,853,092 A | 12/1974 | Amos et al. |
| 3,854,703 A | 12/1974 | Gibbs et al. |
| 3,873,079 A | 3/1975 | Kuus |
| 3,876,297 A | 4/1975 | Appeldorn et al. |
| 3,909,203 A | 9/1975 | Young et al. |
| RE28,585 E | 10/1975 | Amos et al. |
| 3,916,157 A | 10/1975 | Roulette et al. |
| 3,916,160 A | 10/1975 | Russo et al. |
| 3,971,917 A | 7/1976 | Maddox et al. |
| 3,976,028 A | 8/1976 | Howells et al. |
| 3,994,594 A | 11/1976 | Sandrock et al. |
| 4,013,038 A | 3/1977 | Rogers et al. |
| 4,018,565 A | 4/1977 | Fletcher, III et al. |
| 4,039,288 A | 8/1977 | Moran |
| 4,066,412 A | 1/1978 | Johnson et al. |
| 4,083,638 A | 4/1978 | Sandrock et al. |
| 4,084,541 A | 4/1978 | Ito |
| 4,092,952 A | 6/1978 | Wilkie et al. |
| 4,100,309 A | 7/1978 | Micklus et al. |
| 4,113,437 A | 9/1978 | Duff et al. |
| 4,115,861 A | 9/1978 | Allington |
| 4,133,642 A | 1/1979 | Nosaka et al. |
| 4,135,883 A | 1/1979 | McNeil et al. |
| 4,159,875 A | 7/1979 | Hauser |
| 4,163,643 A | 8/1979 | Hunter et al. |
| 4,200,056 A | 4/1980 | Johnson |
| 4,200,607 A | 4/1980 | Suzuki |
| 4,227,810 A | 10/1980 | Sandrock et al. |
| 4,245,967 A | 1/1981 | Busselet |
| 4,263,504 A | 4/1981 | Thomas |
| 4,281,387 A | 7/1981 | Kraft et al. |
| 4,286,146 A | 8/1981 | Uno et al. |
| RE30,730 E | 9/1981 | Duff |
| 4,298,571 A | 11/1981 | DiFulvio et al. |
| 4,323,537 A | 4/1982 | Mody |
| 4,338,279 A | 7/1982 | Orimo et al. |
| 4,346,056 A | 8/1982 | Sakurada |
| 4,371,498 A | 2/1983 | Scordato et al. |
| 4,404,641 A | 9/1983 | Bazarnik |
| 4,406,547 A | 9/1983 | Aihara |
| 4,413,584 A | 11/1983 | DiMaggio et al. |
| 4,447,395 A | 5/1984 | Englar et al. |
| 4,455,280 A | 6/1984 | Shinohara et al. |
| 4,467,073 A | 8/1984 | Creasy |
| 4,467,603 A | 8/1984 | Wilson |
| 4,488,679 A | 12/1984 | Bockholt et al. |
| 4,510,169 A | 4/1985 | Linner |
| 4,517,160 A | 5/1985 | Galle et al. |
| 4,528,159 A | 7/1985 | Liston |
| 4,531,455 A | 7/1985 | Palmer |
| 4,539,632 A | 9/1985 | Hansen et al. |
| 4,558,946 A | 12/1985 | Galle et al. |
| 4,567,748 A | 2/1986 | Klass et al. |
| 4,571,699 A | 2/1986 | Herzog et al. |
| 4,585,622 A | 4/1986 | Bowe et al. |
| 4,609,017 A | 9/1986 | Coulter et al. |
| 4,624,588 A | 11/1986 | Bivin |
| 4,634,576 A | 1/1987 | Galle et al. |
| 4,634,850 A | 1/1987 | Pierce et al. |
| 4,643,879 A | 2/1987 | Hanaway |
| 4,647,432 A | 3/1987 | Wakatake |
| 4,647,543 A | 3/1987 | Stöcker |
| 4,651,671 A | 3/1987 | Pedersen |
| 4,656,006 A | 4/1987 | Assmann et al. |
| 4,664,526 A | 5/1987 | Scheffler et al. |
| 4,675,299 A | 6/1987 | Witty et al. |
| 4,678,752 A | 7/1987 | Thorne et al. |
| 4,678,894 A | 7/1987 | Shafer |
| 4,681,741 A | 7/1987 | Hanaway |
| 4,683,120 A | 7/1987 | Meserol et al. |
| 4,688,517 A | 8/1987 | Hollman |
| 4,692,308 A | 9/1987 | Riley et al. |
| 4,692,603 A | 9/1987 | Brass et al. |
| 4,695,430 A | 9/1987 | Corville et al. |
| 4,708,886 A | 11/1987 | Nelson |
| 4,719,087 A | 1/1988 | Hanaway |
| 4,727,033 A | 2/1988 | Hijikata et al. |
| 4,728,783 A | 3/1988 | Brass et al. |
| 4,728,959 A | 3/1988 | Maloney et al. |
| 4,729,661 A | 3/1988 | Bell |
| 4,738,824 A | 4/1988 | Takeuchi |
| 4,751,186 A | 6/1988 | Baisch et al. |
| 4,754,127 A | 6/1988 | Brass et al. |
| 4,764,342 A | 8/1988 | Kelln et al. |
| 4,774,055 A | 9/1988 | Wakatake et al. |
| 4,781,891 A | 11/1988 | Galle et al. |
| 4,782,221 A | 11/1988 | Brass et al. |
| 4,794,239 A | 12/1988 | Allais |
| 4,795,613 A | 1/1989 | Azuma et al. |
| 4,795,710 A | 1/1989 | Muszak et al. |
| 4,797,938 A | 1/1989 | Will |
| 4,800,762 A | 1/1989 | Sugava |
| 4,808,380 A | 2/1989 | Minekane |
| 4,815,978 A | 3/1989 | Mazz et al. |
| 4,817,916 A | 4/1989 | Rawstron |
| 4,824,641 A | 4/1989 | Williams |
| 4,844,887 A | 7/1989 | Galle et al. |
| 4,847,208 A | 7/1989 | Bogen |
| 4,849,177 A | 7/1989 | Jordan |
| 4,855,109 A | 8/1989 | Muraishi et al. |
| 4,855,110 A | 8/1989 | Marker et al. |
| 4,865,811 A | 9/1989 | Newton et al. |
| 4,868,129 A | 9/1989 | Gibbons et al. |
| 4,869,114 A | 9/1989 | Kido et al. |
| 4,871,682 A | 10/1989 | Mazza |
| 4,873,877 A | 10/1989 | Harris |
| 4,874,936 A | 10/1989 | Chandler et al. |
| 4,886,590 A | 12/1989 | Tittle |
| 4,896,029 A | 1/1990 | Chandler et al. |
| 4,900,513 A | 2/1990 | Barker et al. |
| 4,919,887 A | 4/1990 | Wakatake |
| 4,924,078 A | 5/1990 | Sant' Anselmo et al. |
| 4,933,147 A | 6/1990 | Hollar et al. |
| 4,935,875 A | 6/1990 | Shah et al. |
| 4,939,354 A | 7/1990 | Priddy et al. |
| 4,939,674 A | 7/1990 | Price et al. |
| 4,943,415 A | 7/1990 | Przybylowicz et al. |
| 4,961,906 A | 10/1990 | Andersen et al. |
| 4,965,049 A | 10/1990 | Lillig et al. |
| 4,967,606 A | 11/1990 | Wells et al. |
| 4,985,206 A | 1/1991 | Bowman et al. |
| 4,986,891 A | 1/1991 | Sarrine et al. |
| 4,988,482 A | 1/1991 | Weston |
| 4,998,010 A | 3/1991 | Chandler et al. |
| 5,031,797 A | 7/1991 | Boris et al. |
| 5,051,238 A | 9/1991 | Umetsu et al. |
| 5,053,609 A | 10/1991 | Priddy et al. |
| 5,059,393 A | 10/1991 | Quenin et al. |
| 5,073,504 A | 12/1991 | Bogen |

| | | | | | |
|---|---|---|---|---|---|
| 5,075,079 A | 12/1991 | Kerr et al. | 5,737,499 A | 4/1998 | Bernstein et al. |
| 5,081,038 A | 1/1992 | Sugaya et al. | 5,758,033 A | 5/1998 | Bernstein et al. |
| 5,102,624 A | 4/1992 | Muraishi | 5,776,414 A | 7/1998 | Itani et al. |
| 5,104,527 A | 4/1992 | Clinkenbeard | 5,798,092 A | 8/1998 | Schmitt-Willich et al. |
| 5,106,583 A | 4/1992 | Raysberg et al. | 5,820,849 A | 10/1998 | Schmitt-Willich et al. |
| 5,118,369 A | 6/1992 | Shamir | 5,839,091 A | 11/1998 | Rhett et al. |
| 5,122,342 A | 6/1992 | McCullochh et al. | 5,854,075 A | 12/1998 | Levine et al. |
| 5,124,536 A | 6/1992 | Priddy et al. | 5,875,286 A | 2/1999 | Bernstein et al. |
| 5,175,086 A | 12/1992 | Takekawa et al. | 5,876,698 A | 3/1999 | Schmitt-Willich et al. |
| 5,180,606 A | 1/1993 | Stokes et al. | 5,885,529 A | 3/1999 | Babson et al. |
| 5,202,552 A | 4/1993 | Little et al. | 5,888,576 A | 3/1999 | Nagano |
| 5,225,325 A | 7/1993 | Miller et al. | 5,888,733 A | 3/1999 | Hyldig-Nielsen et al. |
| 5,229,074 A | 7/1993 | Heath et al. | 5,888,876 A | 3/1999 | Shiozawa et al. |
| 5,232,664 A | 8/1993 | Krawzak et al. | 5,930,461 A | 7/1999 | Bernstein et al. |
| 5,250,262 A | 10/1993 | Heidt et al. | 5,945,341 A | 8/1999 | Howard, III |
| 5,281,395 A | 1/1994 | Markart et al. | 5,947,167 A | 9/1999 | Bogen et al. |
| 5,289,385 A | 2/1994 | Grandone | 5,948,359 A | 9/1999 | Kalra et al. |
| 5,311,426 A | 5/1994 | Donohue et al. | 5,958,341 A | 9/1999 | Chu |
| 5,316,319 A | 5/1994 | Suggs | 5,963,368 A | 10/1999 | Domanik et al. |
| 5,316,452 A | 5/1994 | Bogen et al. | 5,965,454 A | 10/1999 | Farmilo et al. |
| 5,316,726 A | 5/1994 | Babson et al. | 5,985,563 A | 11/1999 | Hyldig-Nielsen et al. |
| 5,316,728 A | 5/1994 | Hayashi et al. | 5,994,071 A | 11/1999 | Ross et al. |
| 5,322,771 A | 6/1994 | Rybski et al. | 6,017,495 A | 1/2000 | Ljungmann |
| 5,331,176 A | 7/1994 | Sant' Anselmo et al. | 6,019,945 A | 2/2000 | Ohishi et al. |
| 5,338,358 A | 8/1994 | Mizusawa et al. | 6,045,759 A | 4/2000 | Ford et al. |
| 5,350,697 A | 9/1994 | Swope et al. | 6,080,363 A | 6/2000 | Takahashi et al. |
| 5,355,304 A | 10/1994 | DeMoranville et al. | 6,083,490 A | 7/2000 | Ellis et al. |
| 5,355,439 A | 10/1994 | Bernstein et al. | 6,092,695 A | 7/2000 | Loeffler |
| 5,355,695 A | 10/1994 | Kawaguchi et al. | 6,093,574 A | 7/2000 | Druyor-Sanchez et al. |
| 5,356,595 A | 10/1994 | Kanamori et al. | 6,096,271 A | 8/2000 | Bogen et al. |
| 5,365,614 A | 11/1994 | Perkins | 6,097,995 A | 8/2000 | Tipton et al. |
| 5,366,896 A | 11/1994 | Margrey et al. | 6,104,483 A | 8/2000 | Sebok et al. |
| 5,369,261 A | 11/1994 | Shamir | 6,110,425 A | 8/2000 | Gao et al. |
| 5,382,511 A | 1/1995 | Stapleton | 6,110,676 A | 8/2000 | Coull et al. |
| 5,395,588 A | 3/1995 | North, Jr. et al. | 6,142,292 A | 11/2000 | Patterson |
| 5,417,213 A | 5/1995 | Prince | 6,169,169 B1 | 1/2001 | Hyldig-Nielsen et al. |
| 5,418,138 A | 5/1995 | Miller et al. | 6,180,061 B1 | 1/2001 | Bogen et al. |
| 5,424,036 A | 6/1995 | Ushikubo | 6,183,693 B1 | 2/2001 | Bogen et al. |
| 5,425,918 A | 6/1995 | Healey et al. | 6,192,945 B1 | 2/2001 | Ford et al. |
| 5,428,740 A | 6/1995 | Wood et al. | 6,193,933 B1 | 2/2001 | Sasaki et al. |
| 5,431,455 A | 7/1995 | Seely | 6,208,771 B1 | 3/2001 | Jared et al. |
| 5,432,056 A | 7/1995 | Hartman et al. | 6,235,476 B1 | 5/2001 | Bergmann et al. |
| 5,439,645 A | 8/1995 | Saralegui et al. | 6,244,474 B1 | 6/2001 | Loeffler |
| 5,439,649 A | 8/1995 | Tseung et al. | 6,245,207 B1 | 6/2001 | Yasuda et al. |
| 5,439,826 A | 8/1995 | Kontorovich | 6,248,590 B1 | 6/2001 | Malachowski |
| 5,446,652 A | 8/1995 | Peterson et al. | 6,281,004 B1 | 8/2001 | Bogen et al. |
| 5,449,622 A | 9/1995 | Yabe et al. | 6,287,772 B1 | 9/2001 | Stefano et al. |
| 5,473,551 A | 12/1995 | Sato et al. | 6,296,809 B1 | 10/2001 | Richards et al. |
| 5,487,975 A | 1/1996 | Miller et al. | 6,310,179 B1 | 10/2001 | Batz et al. |
| 5,544,650 A | 8/1996 | Boon et al. | 6,319,470 B1 | 11/2001 | Lefevre et al. |
| 5,549,848 A | 8/1996 | Zeheb et al. | 6,327,395 B1 | 12/2001 | Hecht et al. |
| 5,552,087 A | 9/1996 | Zeheb et al. | 6,335,208 B1 | 1/2002 | Lowry |
| 5,573,727 A | 11/1996 | Keefe | 6,349,264 B1 | 2/2002 | Rhett et al. |
| 5,595,707 A | 1/1997 | Copeland et al. | 6,352,861 B1 | 3/2002 | Copeland et al. |
| 5,601,650 A | 2/1997 | Goldbecker et al. | 6,358,682 B1 | 3/2002 | Jaffee et al. |
| 5,602,674 A | 2/1997 | Weissman et al. | 6,387,326 B1 | 5/2002 | Edwards et al. |
| 5,612,524 A | 3/1997 | Sant' Anselmo et al. | 6,388,061 B1 | 5/2002 | Bergmann et al. |
| 5,645,114 A | 7/1997 | Bogen et al. | 6,395,562 B1 | 5/2002 | Hammock et al. |
| 5,646,046 A | 7/1997 | Fischer et al. | 6,403,036 B1 | 6/2002 | Rodgers et al. |
| 5,649,537 A | 7/1997 | Anelli et al. | 6,403,931 B1 | 6/2002 | Showalter et al. |
| 5,650,136 A | 7/1997 | Platzek et al. | 6,405,609 B1 | 6/2002 | Richards et al. |
| 5,650,327 A | 7/1997 | Copeland et al. | 6,408,931 B1 | 6/2002 | Tilak |
| 5,654,199 A | 8/1997 | Copeland et al. | 6,414,133 B1 | 7/2002 | Dietz-Band et al. |
| 5,654,200 A | 8/1997 | Copeland et al. | 6,416,713 B1 | 7/2002 | Ford et al. |
| 5,656,493 A | 8/1997 | Mullis et al. | 6,420,916 B1 | 7/2002 | Freeman |
| 5,675,715 A | 10/1997 | Bernstein et al. | 6,426,794 B1 | 7/2002 | Trainoff |
| 5,677,966 A | 10/1997 | Doerrer et al. | 6,444,170 B1 | 9/2002 | Heid et al. |
| 5,681,543 A | 10/1997 | Schmitt-Willich et al. | 6,472,217 B1 | 10/2002 | Richards et al. |
| 5,695,739 A | 12/1997 | Schmitt-Willich et al. | 6,498,037 B1 | 12/2002 | Carey et al. |
| 5,696,887 A | 12/1997 | Bernstein et al. | 6,509,193 B1 | 1/2003 | Tajima |
| 5,723,092 A | 3/1998 | Babson | 6,534,008 B1 | 3/2003 | Angros |
| 5,733,528 A | 3/1998 | Felder et al. | 6,537,818 B2 | 3/2003 | Richards et al. |
| 5,737,449 A | 4/1998 | Lee | 6,541,261 B1 | 4/2003 | Bogen et al. |

| | | | | | |
|---|---|---|---|---|---|
| 6,544,798 B1 | 4/2003 | Christensen et al. | AU | 2638995 A1 | 12/1995 |
| 6,548,822 B1 | 4/2003 | Morris et al. | DE | 69417909 T2 | 11/1999 |
| 6,582,962 B1 | 6/2003 | Richards et al. | EP | 0285851 A2 | 10/1988 |
| 6,594,537 B1 | 7/2003 | Bernstein et al. | EP | 0290018 A2 | 11/1988 |
| 6,635,225 B1 | 10/2003 | Thiem et al. | EP | 0310303 A1 | 4/1989 |
| 6,699,710 B1 | 3/2004 | Kononen et al. | EP | 0325101 A1 | 7/1989 |
| 6,735,531 B2 | 5/2004 | Rhett et al. | EP | 0600939 B1 | 6/1994 |
| 6,800,249 B2 | 10/2004 | de la Torre-Bueno | EP | 0722363 B1 | 7/1996 |
| 6,872,901 B2 | 12/2004 | Copeland et al. | EP | 0881481 A1 | 12/1998 |
| 6,855,559 B1 | 2/2005 | Christensen et al. | ES | 2160486 A1 | 11/2001 |
| 6,943,029 B2 | 9/2005 | Copeland et al. | FR | 2239167 | 7/1973 |
| 2001/0006417 A1 | 7/2001 | Modlin et al. | GB | 2216 259 | 3/1988 |
| 2001/0010936 A1 | 8/2001 | Richards et al. | GB | 2218514 A | 3/2003 |
| 2001/0037072 A1 | 11/2001 | Virtanen | JP | 54014287 A | 2/1979 |
| 2001/0044124 A1 | 11/2001 | Bacus | JP | 55107957 | 8/1980 |
| 2001/0049114 A1 | 12/2001 | Bacus | JP | 63240688 A2 | 10/1988 |
| 2001/0055799 A1 | 12/2001 | Baunoch et al. | JP | 6504115 T2 | 5/1994 |
| 2002/0001849 A1 | 1/2002 | Copeland et al. | JP | 8500922 T2 | 1/1996 |
| 2002/0009391 A1 | 1/2002 | Marquiss et al. | JP | 8506888 T2 | 7/1996 |
| 2002/0019001 A1 | 2/2002 | Light | JP | 9503304 T2 | 3/1997 |
| 2002/0031445 A1 | 3/2002 | Theim et al. | WO | WO 85/03571 | 8/1985 |
| 2002/0051735 A1 | 5/2002 | Dorenkamp et al. | WO | WO 86/02163 A1 | 4/1986 |
| 2002/0054829 A1 | 5/2002 | Dalkidis et al. | WO | WO 87/00086 | 1/1987 |
| 2002/0057992 A1 | 5/2002 | Eckert et al. | WO | WO 87/00280 A1 | 1/1987 |
| 2002/0072122 A1 | 6/2002 | Copeland et al. | WO | WO 87/06695 A1 | 11/1987 |
| 2002/0076351 A1 | 6/2002 | Wernz et al. | WO | WO 88/02866 | 4/1988 |
| 2002/0091593 A1 | 7/2002 | Fowler | WO | WO 8802865 | 4/1988 |
| 2002/0098118 A1 | 7/2002 | Eckert et al. | WO | WO 89/01616 | 2/1989 |
| 2002/0098595 A1 | 7/2002 | Lubman et al. | WO | WO 91/13335 | 9/1991 |
| 2002/0110494 A1 | 8/2002 | Lemme et al. | WO | WO 92/01919 A1 | 2/1992 |
| 2002/0111743 A1 | 8/2002 | Gropp | WO | WO 93/03451 A1 | 2/1993 |
| 2002/0114733 A1 | 8/2002 | Copeland et al. | WO | WO 95/10035 A2 | 4/1995 |
| 2002/0116132 A1 | 8/2002 | Rhett et al. | WO | WO 95/10035 A3 | 4/1995 |
| 2002/0176801 A1 | 11/2002 | Giebeler et al. | WO | WO 95/28179 A1 | 10/1995 |
| 2002/0178547 A1 | 12/2002 | Shofner et al. | WO | WO 95/32741 A1 | 12/1995 |
| 2002/0182628 A1 | 12/2002 | Dietz-Band et al. | WO | WO 95/33240 | 12/1995 |
| 2003/0003537 A1 | 1/2003 | Fischer et al. | WO | WO 97/23732 A1 | 7/1997 |
| 2003/0022391 A1 | 1/2003 | Richards et al. | WO | WO 97/26541 A1 | 7/1997 |
| 2003/0032048 A1 | 2/2003 | Kim et al. | WO | WO 94/06080 | 3/1999 |
| 2003/0043963 A1 | 3/2003 | Yamagami et al. | WO | WO 99/34190 A1 | 7/1999 |
| 2003/0049171 A1 | 3/2003 | Tamura et al. | WO | WO 99/43434 A1 | 9/1999 |
| 2003/0059790 A1 | 3/2003 | Jaffee et al. | WO | WO 99/44031 A1 | 9/1999 |
| 2003/0087443 A1 | 5/2003 | Pressman et al. | WO | WO 99/49295 A1 | 9/1999 |
| 2003/0099573 A1 | 5/2003 | Tseung et al. | WO | WO 99/55916 A1 | 11/1999 |
| 2003/0119200 A1 | 6/2003 | Taft et al. | WO | WO 99/57309 A1 | 11/1999 |
| 2003/0124729 A1 | 7/2003 | Christensen et al. | WO | WO 00/02030 A1 | 1/2000 |
| 2003/0162221 A1 | 8/2003 | Bader et al. | WO | WO 00/02660 A1 | 1/2000 |
| 2003/0200111 A1 | 10/2003 | Damji | WO | WO 00/36393 A2 | 6/2000 |
| 2003/0215357 A1 | 11/2003 | Malterer et al. | WO | WO 01/02859 A1 | 1/2001 |
| 2003/0215936 A1 | 11/2003 | Kallioniemi et al. | WO | WO 01/02861 A1 | 1/2001 |
| 2004/0002163 A1 | 1/2004 | Reinhardt et al. | WO | WO 0106255 A | 1/2001 |
| 2004/0005244 A1 | 1/2004 | Thiem | WO | WO 01/07890 A2 | 2/2001 |
| 2004/0033163 A1 | 2/2004 | Tseung et al. | WO | WO 01/51909 A1 | 7/2001 |
| 2004/0266015 A1 | 12/2004 | Favuzzi et al. | WO | WO 01/55346 A3 | 8/2001 |
| 2005/0038676 A1 | 2/2005 | Showalter et al. | WO | WO 01/68269 A1 | 9/2001 |
| 2005/0064535 A1 | 3/2005 | Favuzzi et al. | WO | WO 01/87487 A2 | 11/2001 |
| 2005/0124028 A1 | 6/2005 | Windeyer et al. | WO | WO 01/87487 A3 | 11/2001 |
| 2005/0159982 A1 | 7/2005 | Showalter et al. | WO | WO 03/045560 A2 | 6/2003 |
| 2006/0045806 A1 | 3/2006 | Winther et al. | WO | WO 03/045560 A3 | 6/2003 |
| 2006/0046298 A1 | 3/2006 | Key et al. | WO | WO 03/052386 A1 | 6/2003 |
| 2006/0063265 A1 | 3/2006 | Welcher et al. | WO | WO 2004/057307 | 7/2004 |
| 2006/0085140 A1 | 4/2006 | Feingold et al. | WO | WO 2004/057308 A1 | 7/2004 |
| 2006/0088928 A1 | 4/2006 | Sweet et al. | WO | WO 2004/058404 A2 | 7/2004 |
| 2006/0088940 A1 | 4/2006 | Feingold et al. | WO | WO 2004/058404 A3 | 7/2004 |
| 2006/0105359 A1 | 5/2006 | Favuzzi et al. | WO | WO 2004/058950 A1 | 7/2004 |
| 2006/0120921 A1 | 6/2006 | Elliot et al. | WO | WO 2004/059284 A2 | 7/2004 |
| 2006/0172426 A1 | 8/2006 | Buchanan et al. | WO | WO 2004/059284 A3 | 7/2004 |
| 2007/0204734 A1 | 9/2007 | Ito et al. | WO | WO 2004/059287 A2 | 7/2004 |
| | | | WO | WO 2004/059287 A3 | 7/2004 |
| | FOREIGN PATENT DOCUMENTS | | WO | WO 2004/059288 A2 | 7/2004 |
| | | | WO | WO 2004/059288 A3 | 7/2004 |
| AU | 7754191 A1 | 2/1992 | WO | WO 2004/059297 A1 | 7/2004 |
| AU | 0644876 B2 | 12/1993 | WO | WO 2004/059441 A2 | 7/2004 |

| | | | |
|---|---|---|---|
| WO | WO 2004/059441 A3 | 7/2004 | |
| WO | WO 2005-084263 A2 | 9/2005 | |

OTHER PUBLICATIONS

Chow et al., "Application of Existing Technology to Meet Increasing Demands for Automated Sample Handling," Clinical Chemistry, 36(9):1579-1582, 1990.
Driscoll et al., "Discreet Automated Chemistry System with Tabeted Reagents," Clinical Chemistry, 29(9): 1609-1615, 1983.
Garza et al., "Bar Codes in the Clinical Laboratory," Clinical Laboratory Science, 4(1): 23-24, Jan./Feb. 1991.
Innis et al., "DNA Sequencing with *Thermus aquaticus* DNA Polymerase and Direct Sequencing of Polymerase Chain Reaction-Amplified DNA," Proc. Natl. Acad. Sci, 85:9436-9440, Dec. 1998.
International Application No. PCT/US03/40520 filed Dec. 19, 2003; Written Opinion.
International Application No. PCT/US03/40974 filed Dec. 19, 2003; Written Opinion.
International Application No. PCT/US03/40880 Written Opinion dated Sep. 28, 2005.
International Preliminary Examination Report, P131WO01, International Application No. PCT/US03/40518 filed Dec. 19, 2003.
International Preliminary Examination Report, P139WO01, International Application No. PCT/US03/40880 filed Dec. 22, 2003.
International Preliminary Examination Report, P140WO01, International Application No. PCT/DK03/00877 filed Dec. 15, 2003.
International Preliminary Examination Report, P142WO01, International Application No. PCT/US03/40519 filed Dec. 19, 2003.
International Preliminary Examination Report, P143WO01, International Application No. PCT/US03/40591 filed Dec. 19, 2003.
International Preliminary Examination Report, P144WO01, International Application No. PCT/US03/41022 filed Dec. 22, 2003.
International Preliminary Examination Report, P145WO01, International Application No. PCT/US03/40520 filed Dec. 19, 2003, mailing date Mar. 27, 2006.
International Preliminary Examination Report, P145WO01, International Application No. PCT/US03/40520 filed Dec. 19, 2003, mailing date May 31, 2005.
International Preliminary Examination Report, P149WO01, International Application No. PCT/US03/40974 filed Dec. 19, 2003.
Lifshitz, M. S, et al., Talking about Technology, Clinical Laboratory Management Review, Jan.-Feb. 1989; 3(1):53-4.
Lindeman et al., "Evaluation of the Automation of the Immunoenzymatic Procedures in a Routine Histo/Cytopathalogical Laboratory," Histopathology, 6:739-746, 1982.
Pearson, L.S., The use of bar coding technology, Medical Device Technology, Mar. 1994.
Rappaport, "If Bar Code Works in Supermarkets, It Should Be Great for Medicine," Pathologist, 39(2): 39-40, 185.
Rocks, B.F. et al., Automatic analysers in clinical biochemistry, B F Rocks et al. 1986 Clin. Phys. Physiol. Meas. 7 1-29.
Saiki et al., "Enzymatic Amplification of β-Globin Genomic Sequences and Restriction Site Analysis for Diagnosis of Sickle Cell Anemial," Science 230:1350-1353, Dec. 20, 1985.
Singer, R. et al., Selection and evaluation of laboratory instrumentation in clinical chemistry: II Guidelines for selection and evaluation, Med Lab Sci. Jan. 1987; 44(1):6-14.
Stark et al., An automated Devide of Immunocytochemistry, Journal of Immunological Methods, 1988, Elsevier, 107, pp. 89-92.
Taylor, C., Creating a bar code chemistry system, Medical Laboratory Observer, 19993 Feb.; 25(2):34-6.
Tilzer et al., "Use of Bar Code Labels on Collection Tubes for Specimen Management in the Clinical Laboratory," Arch Pathol Lab Med, 112:1201-1202, Dec. 1988.
U.S. Appl. No. 11/119,417, filed Apr. 30, 2005, Method and Apparatus for Pretreatment of Biological Samples.
United States District Court, District of Arizona, CV03-92 TUC-RCC, *Ventana Medical* vs *Biogenix Laboratories* Reporter's Transcript of Proceedings (Markman Hearing) before Honorable Raner C. Collins, Aug. 11, 2005.
United States District Court, District of Arizona, CV03-92 TUC-RCC, *Ventana Medical* vs *Biogenix Laboratories*, Judgment in a Civil Case, Oct. 19, 2005.
United States District Court, District of Arizona, CV03-92 TUC-RCC, *Ventana Medical* vs *Biogenix Laboratories*, Order and Opinion on Motion, Aug. 23, 2005.
United States District Court, District of Arizona, CV03-92 TUC-RCC, *Ventana Medical* vs *Biogenix Laboratories*, Order filed Oct. 4, 2005.
United States District Court, District of Arizona, CIV 02117 TUC (RCC), *Ventana v. Cytologix*, Plaintiff's Memorandum in Support of Petition for Temporary Restraining Order and Permanent Injunction filed Mar. 2002.
United States District Court, District of Arizona, *Ventana v. Cytologix*, CIV 02117 TUC (WDB) Ventana's Reply in Support of its Motion for Preliminary Relief filed Jun. 2002.
United States District Court, District of Arizona, *Ventana v. Cytologix*, CIV 02117 TUC (WDB) Defendant's Surreply in Opposition to Plaintiffs Motion for Preliminary Injunctive Relief filed Jul. 2002.
United States District Court, District of Arizona, *Ventana v. Cytologix*, CIV02117 TUC (RCC) Plaintiff's Motion for Temporary Restraining Order filed Mar. 2002.
United States District Court, District of Arizona, *Ventana v. Dakocytomation California*, CIV041522 (GMS) Order Construing the Terms of U.S. Patent No. 6,827,901 dated Dec. 13, 2005.
United States District Court, District of Massachusetts, *Vision Biosystems (USA) Trading v. Ventana Medical Systems*, CIV 03CV10391GAO, Declaration of Richard Wydeven in Support of Plaintiff's Motion for Summary Judgment of Non-Infringement Based on Collateral Estoppel, filed Oct. 7, 2005.
United States District Court, District of Massachusetts, *Vision Biosystems (USA ) Trading v. Ventana Medical Systems*, CIV 03CV10391GAO, Defendant Ventana Medical Systems, Inc.'s Memorandum in Opposition to Vision's Motion for Summary Judgment of Non-Infringement Based on Collateral Estoppel, filed Oct. 21, 2005.
United States District Court, District of Massachusetts, *Vision Biosystems (USA) Trading v. Ventana Medical Systems*, CIV 03CV10391GAO, Defendant Ventana Medical Systems, Inc.'s Statement of Material Facts in Dispute, in Opposition to Vision's Motion for Summary Judgment of Non-Infringement Based on Collateral Estoppel, filed Oct. 21, 2005.
United States District Court, District of Massachusetts, *Vision Biosystems (USA ) Trading v. Ventana Medical Systems*, CIV 03CV10391GAO, Defendant's Statement of Material Facts in Dispute, in Opposition to Plaintiff's Motion for Summary Judgment of Non-Infringement of the 861 Patent, filed Jan. 15, 2004.
United States District Court District of Massachusetts, *Vision Biosystems (USA ) Trading v. Ventana Medical Systems*, CIV 03CV10391GAO, Memorandum and Order filed Sep. 30, 2004.
United States District Court, District of Massachusetts, *Vision Biosystems (USA ) Trading v. Ventana Medical Systems*, CIV 03CV10391GAO, Plaintiff's Memorandum in Support of its Motion for Summary Judgment of Non-Infringement Based on Collateral Estoppel, filed Oct. 7, 2005.
United States District Court, District of Massachusetts, *Vision Biosystems (USA ) Trading v. Ventana Medical Systems*, CIV 03CV10391GAO, Plaintiff's Motion for Summary Judgment of Non-Infringement Based on Collateral Estoppel, filed Oct. 7, 2005.
United States District Court District of Massachusetts, *Vision Biosystems (USA ) Trading v. Ventana Medical Systems*, CIV 03CV10391GAO, Plaintiff's Statement of Undisputed Facts in Support of its Motion for Summary Judgment of Non-Infringement Based on Collateral Estoppel, filed Oct. 7, 2005.
United States District Court, Eastern District of Massachusetts, *Vision Biosystems (USA ) Trading v. Ventana Medical Systems*, CIV 03CV10391GAO, Defendant's Memorandum in Opposition to Plaintiff's Motion for Summary Judgment of Non-Infringement, and in Support of Defendant's Cross-Motion for Summary Judgment of Infringement of the 861 Patent, filed Jan. 15, 2004.
United States District Court, Eastern District of Massachusetts, *Vision Biosystems (USA ) Trading v. Ventana Medical Systems*, CIV 03CV10391GAO, Defendant's Statement of Undisputed Facts in Support of its Cross-Motion for Summary Judgment of Infringement of the 861 Patent filed Jan. 2004.

U.S. Appl. No. 07/488,601, "Automated Biological Reaction Apparatus" filed Mar. 2, 1990.

U.S. Appl. No. 07/924,052, "Aumated Biological Reaction Apparatus" filed Aug. 31, 1992.

U.S. Appl. No. 60/487,998, "An Interface Point Server," filed Jul. 17, 2003, 52 pages.

U.S. Appl. No. 10/054,535, Entitled Automated Biological Reaction Apparatus, now Patent No. 6,943,029, the entire wrapper.

U.S. Appl. No. 60/435,601, filed Dec. 20, 2002.

Supplementary European Search Report, EP 0539379 entitled "Automatic Tissue Staining for Immunohistochemistry," 4 pages.

12 Most Frequently Asked Questions About Thermoelectric Cooling in: Tellurex Corporation, accessed Oct. 27, 2004, http://www.tellurex.com/12most.html.

U.S. Appl. No. 11/156,760, filed Jun. 20, 2005, entitled "Method and Apparatus for Automated Pre-Treatment and Processing of Biological Samples," 126 pages.

METHOD AND SYSTEM FOR PRETREATMENT OF TISSUE SLIDES

This application is a continuation of application Ser. No. 10/731,316, filed Dec. 8, 2003 now U.S. Pat. No. 7,648,678, which claims the benefit of U.S. Provisional Application No. 60/435,601, filed Dec. 20, 2002, the entire disclosures of which are incorporated herein by reference.

BACKGROUND

The present invention relates to a method and an apparatus for automatic staining at least one tissue sample accommodated on a slide by applying reagents in a sequence according to a staining protocol, wherein at least one slide may be provided in a slide rack.

This application relates to the field of sample processing systems and methods of processing samples. The present invention may be directed to the automated processing, treatment, or even staining of samples arranged on carriers, such as microscope slides, and in some embodiments, directed to the continuous or batch processing of samples and carriers, as well as washing elements of a sampling system. Embodiments may further relate to control systems for sample processing and data acquisition, data maintenance, and data retrieval for sample processing. Applications to which the present invention may especially relate include immunohistochemistry, in-situ hybridization, fluorescent in-situ hybridization, special staining, and microarrays, as well as potentially other chemical and biological applications.

Sample processing in immunohistochemical (IHC) applications and in other chemical and biological analyses may require one or a number of various processing sequences or protocols as part of an analysis of one or more samples. The sample processing sequences or protocols may be defined by the individual or organization requesting an analysis, such as a pathologist or histologist of a hospital, and may be further defined by the dictates of a particular analysis to be performed.

In preparation for sample analysis, a biological sample may be acquired by known sample acquisition techniques and may comprise, for example in IHC applications, tissues generally or even in some applications one or a plurality of isolated cells, such as in microarray samples, and may be presented on a sample carrier such as a microscope slide. Furthermore, the sample may be presented on the carrier variously and potentially in some form of preservation. As one example, a sample such as a layer or slice of skin may be preserved in formaldehyde and presented on a carrier with one or more paraffin or other chemical layers overlying the sample.

Immunologic applications, for example, may require processing sequences or protocols that comprise steps such as deparaffinization, target retrieval, and staining, especially for in-situ hybridization (ISH) techniques. Previously, in some applications, these steps may have been performed manually, potentially creating a time-intensive protocol and necessitating personnel to be actively involved in the sample processing. Attempts have been made to automate sample processing to address the need for expedient sample processing and a less manually burdensome operation. However, such previous efforts may not have fully addressed the needs for an automated sample processing system. Previous efforts to automate sample processing may be deficient in several aspects that prevent more robust automated sample processing, such as: the lack of sufficient computer control and monitoring of sample processing; the lack of information sharing for processing protocol and processing status, especially for individual samples; the lack of diagnostic capabilities; and the lack of real-time or adaptive capabilities for multiple sample batch processing.

Past efforts at automated sample processing for samples presented on carriers such as slides, such as U.S. Pat. No. 6,352,861 and U.S. Pat. No. 5,839,091, have not afforded the various advantages and other combinations of features as presented herein.

The tissue samples may be prepared before the staining can be performed. The tissue slides may be subjected to a pretreatment process depending on the type of staining process that may be performed on the tissue. This pretreatment could include a deparafinization or a target retrieval. The preparation of the tissues on the slides may often be carried out manually in the laboratory before they are loaded into the automatic staining instrument. This pretreatment may include immersing the slide in a buffer or other types of processing liquid for a predetermined amount of time and temperature.

However, this manual preparation may be cumbersome and the pretreatment may be insufficient, since it may be critical that the amount of time and the temperature of the liquid must be observed very precisely in order to achieve the correct pretreatment result.

SUMMARY OF INVENTION

It is an object of the invention to provide an automatic pretreatment of the slides in an automatic staining apparatus so that the entire tissue sample processing may be performed in a single automatic apparatus.

The invention consists of a method of treatment of at least one tissue sample accommodated on a slide in an automated staining apparatus, the method comprising the steps of: providing at least one slide having a tissue sample which may even be in a predetermined slide location, a slide may be in a substantially horizontal position; pivoting at least one slide to a substantially vertical position; immersing a substantially vertically oriented slide into a fluid containment element or even in a dip tank for a processing time which may be predetermined. In embodiments, the slide may be located in a slide rack, a plurality of slides may be provided in a slide rack, and even the slides may be individually pivotable.

An object may be also achieved by an apparatus for automatic staining at least one tissue sample accommodated on a slide by applying a predetermined amount of reagents in a sequence according to a staining protocol, wherein at least one slide may be provided in a slide rack assembly or even a slide rack, wherein the slide rack assembly may comprise means for pretreatment of the tissue sample on a slide after the slide may be provided in the slide rack assembly or more broadly a pretreatment element. Said means for pretreatment of tissue samples may include a fluid containment element or even a dip tank which may be provided in a slide rack assembly; a slide rack holder, and means for pivoting the slides provided in the slide rack holder to a vertical position or more broadly a vertical slide positioner adapted to pivot at least one slide in a vertical position and means for immersing the vertical slide into the dip tank or more broadly a slide immerser element adapted to immerse at least one slide in a fluid containment element.

By pivoting the slides from a horizontal to a vertical position, an automated method and apparatus for carrying out the pretreatment in the automated staining apparatus may be provided. A pivoting of slides may ensure an appropriate orientation of the slides for both the pretreatment and the staining processes.

By the present invention, the preparation of the tissue samples on the slides may be integrated in an automatic staining apparatus, so that a tissue sample once it may be accommodated on a slide can be loaded into a staining apparatus wherein both the pretreatment and the staining protocols may be performed automatically in the apparatus.

In embodiments, a selected processing liquid may be supplied from at least one supply tank into a fluid containment element or even a dip tank. The steps of filling and draining a dip tank may be controlled by a control system of the apparatus which may ensure that the slides are subjected to the appropriate pretreatment steps according to information concerning this in the staining protocol.

In other embodiments, the liquid may be transferred from a supply tank to a transfer tank and onwards to a dip tank. The apparatus may comprise pneumatic means for transferring processing liquid, or more broadly the present invention may include a pneumatic element adapted to transfer liquid from a supply tank to a transfer tank and from the transfer tank to the dip tank and draining liquid or a drain element adapted to remove liquid from the dip tank to the transfer tank and from said transfer tank to a waste collection tank. An advantage achieved by transferring the liquids by a pneumatic system may be that the at least one transfer tank, the supply tank and the waste tank may be positioned outside the apparatus, and may hereby allow for an increased capacity as there are no dimensional constrains on the tank sizes. Furthermore, in an embodiment of the invention it may be possible to subject the immersed slide to a series of fluids which are sequentially filled and drained from the dip tank, since the system may easily be adapted to contain several supply tanks containing different liquids and similarly also several waste tanks so that it may be possible to sort the waste.

In an embodiment, a fluid containment element or even a dip tank may be provided with a heating member for heating the processing liquid contained in a fluid containment element or even a dip tank, and the heating member may advantageously be capable of heating the dip tank content to an elevated temperature of at least 95° C., or even at least 120° C. Hereby, the temperature of the fluid in the dip tank may be heated up to 120° C. or even as high as 150° C. and kept at this temperature for between 10 to 20 minutes without any sign of boiling. In an embodiment, the heating member may be adapted to heat the fluid to a temperature of 95° C. for 40 minutes or more for performing a target retrieval process.

According to an embodiment of the invention, the at least one vertical slide may be immersed into the tank by lowering the slide rack holder or even a slide holder and immersing at least one slide into a fluid containment element or even a dip tank after at least one slide may be pivoted to a vertical position. Hereby, a compact dip tank arrangement and slide rack holder lay out may be achieved.

The method of treatment of tissue could be a pretreatment of the tissue sample. However, by the invention it may be realized that other types of treatment may be performed on the tissue sample on the slide in a vertical position, such as rinsing the slides. Other processes that may be performed by an apparatus according to the invention include deparaffinization, target retrieval processes, or other processes of the tissue sample.

According to embodiments of the present invention, a fluid containment element or even a dip tank may be an elongated tank having an upper opening slot which may allow vertically oriented slides to be inserted into the container for treatment. Hereby, the volume of a fluid containment element or even a dip tank and thereby the amount of processing fluid needed may be minimized.

In other embodiments, the apparatus may include means for recycling the drained liquid for re-use in a later pretreatment process of slides or more broadly a liquid recycle element adapted to provide recycled liquid. Hereby, the amount of fluids used for the operation of the apparatus, i.e. a pretreatment and the rinsing of the tissue slides, may be minimized and may result in an easier waste handling and a reduction in costs.

In an embodiment of the invention, a slide rack assembly may be provided in a drawer assembly which may be retracted from the apparatus for loading and unloading of slides. The drawer assembly may cooperate with a fluid containment element or even a dip tank in the drawer receiving means of the apparatus, a dip tank may be capable of simultaneous processing of a plurality of slides accommodated in a plurality of slide holders in the slide rack assembly or even a slide rack. The drawer assembly may provide an apparatus with a great flexibility in use, as slides may be loaded or unloaded from one drawer while the slides in the other drawers may be processed independent thereof. Furthermore, the use of drawers may make it easy to operate an automatic staining system. A fluid containment element or even dip tanks for each of the drawers may be connected to common supply and waste tanks which advantageously may be arranged outside the apparatus.

BRIEF DESCRIPTION OF THE FIGURES

The invention is described with reference to various embodiments with reference to the drawings, in which.

DETAILED DESCRIPTION OF PREFERRED EMBODIMENTS

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should further be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
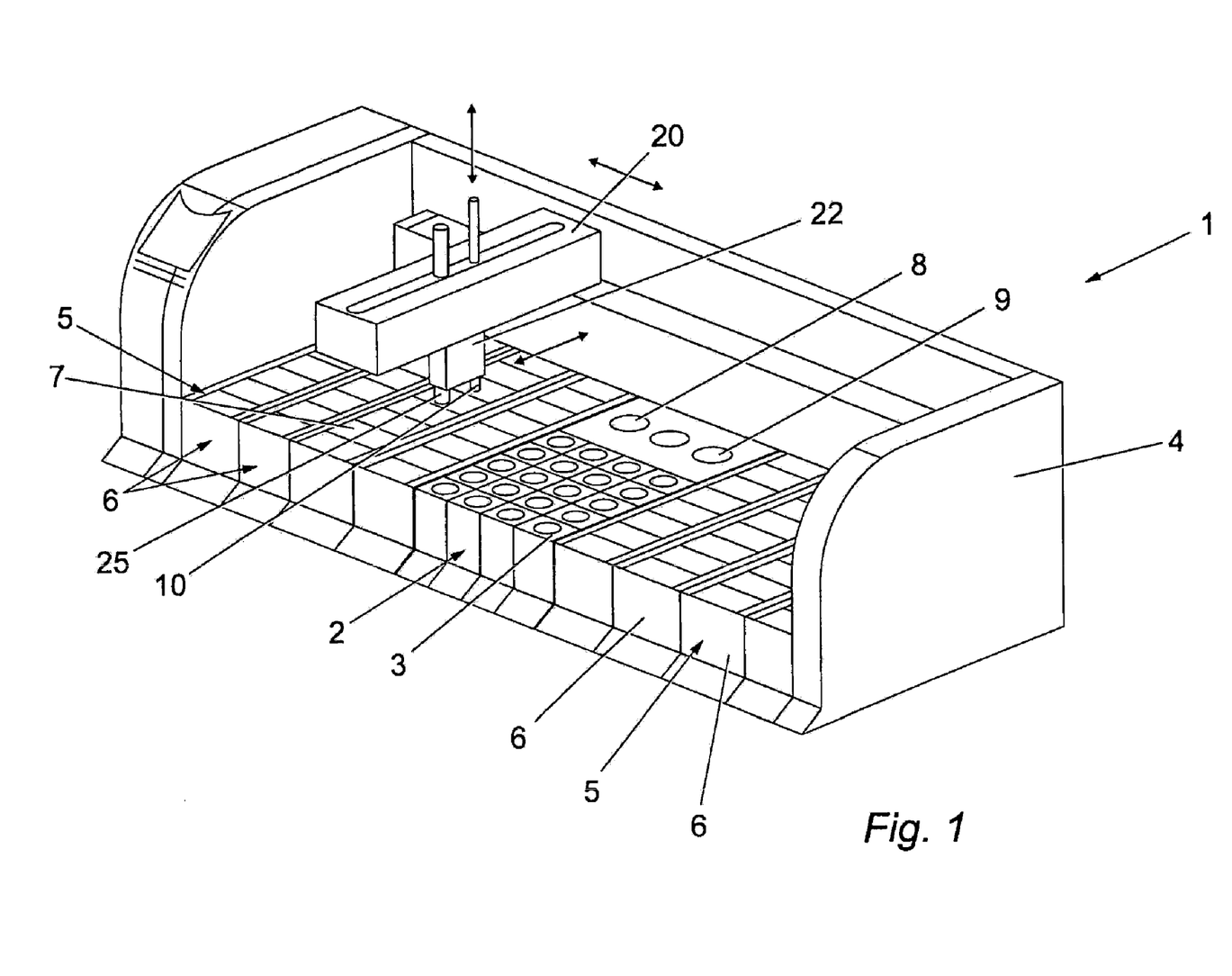
FIG. 1 is a schematic perspective view of a staining apparatus according to the preferred embodiment of the invention.
Figure 2:
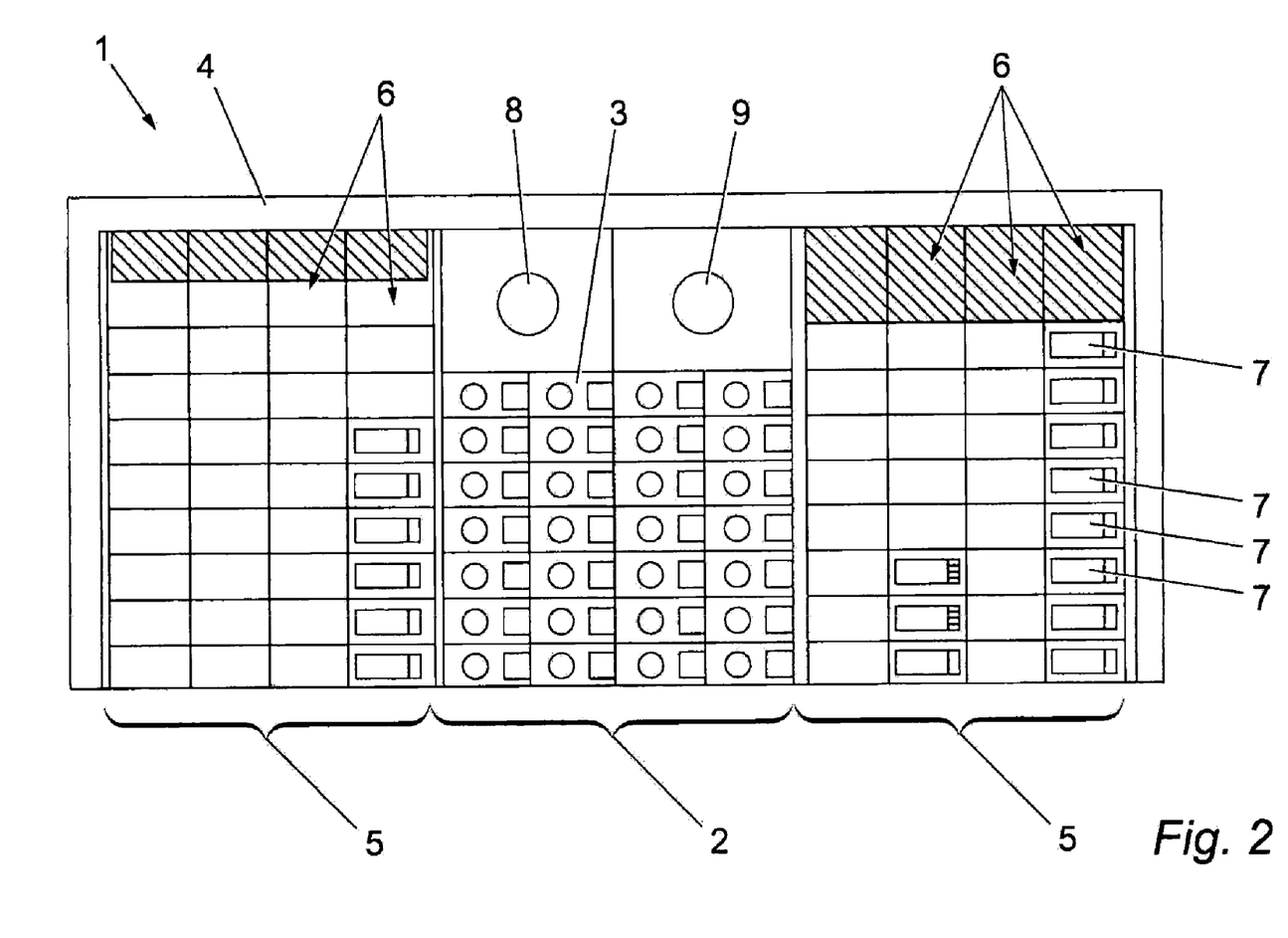
FIG. 2 is a top view of the work area in the staining apparatus shown in FIG. 1.

A staining apparatus 1 according to an embodiment of the invention is shown in FIGS. 1 and 2. The staining apparatus 1 may comprise a rectangular frame 4 surrounding a reagent station 2 comprising an array of reagent bottle compartments wherein each compartment a reagent vial 3 may be placed, and a first and second slide sections 5 wherein a number of separate rack assemblies 6 may be placed, and where each rack assembly 6 accommodates a number of microscope slides 7 mounted side by side in a rack assembly 6. In the embodiment shown, each rack may hold up to 8 slides, but the rack may be designed to hold any suitable number of slides. With eight racks arranged side by side, the shown embodiments may hold up to 64 slides 7 each having a sample, e.g. a tissue mounted on the upper side of the slide, so that at least one reagent may be applied from above to the sample on each slide.

A robot arm 20 for moving a probe 10 in X and Y (as well as Z) direction as indicated by the arrows X and Y may be arranged above the frame 4 of the staining apparatus. The robot arm 20 may therefore position the probe 10 above all reagent vials 3 as well as above all the microscope slides 7, and may further operate the probe 10 to aspirate portions of reagent contained in any of the vials 3, to transfer the portion of reagent and apply it to any of the slides 7 in order to provide a selected staining or treatment of the sample on each slide 7. By use of suitable control means e.g. a computer (not shown) having the appropriate software and input data for the purpose, this staining apparatus 1 may be able to automatically staining or treating samples requiring different staining or treatment reagents and processes.

As shown in FIG. 1, the probe 10 may be accommodated in a robotic head 22 and may be manipulated by the robot arm 20. The probe 10 may be raised to an upper position (in a Z direction) where it may be clear of the vials 3 underneath the probe 10, but the robot may include means in the robotic head 22 for lowering the probe 10, or more broadly a lowering element, in order to dip the probe tip into the content of a selected reagent vial 3 and to aspirate a selected amount of reagent for the selected staining or treatment process. The robotic head 22 may be also provided with a CCD camera 25 pointing downwards. The camera may be utilized to determine status information of the slides and the reagent bottles and other features of the apparatus in the work area, for example reading a code provided on a reagent container to determine the reagent type and the reagent location within the system. The camera may also determine status of the tissue sample carriers, for example the location of a particular slide, informational indicia, such as a code, that indicate information about the tissue sample presented on the slide or the processing protocol to be performed.

In an embodiment, the staining apparatus 1 of the present invention may further comprise a probe washing station 8 and a reagent mixer 9, and the robot arm 20 may be furthermore arranged to transfer the probe to the washing station 8 as well as to the reagent mixer 9.

Figure 3:
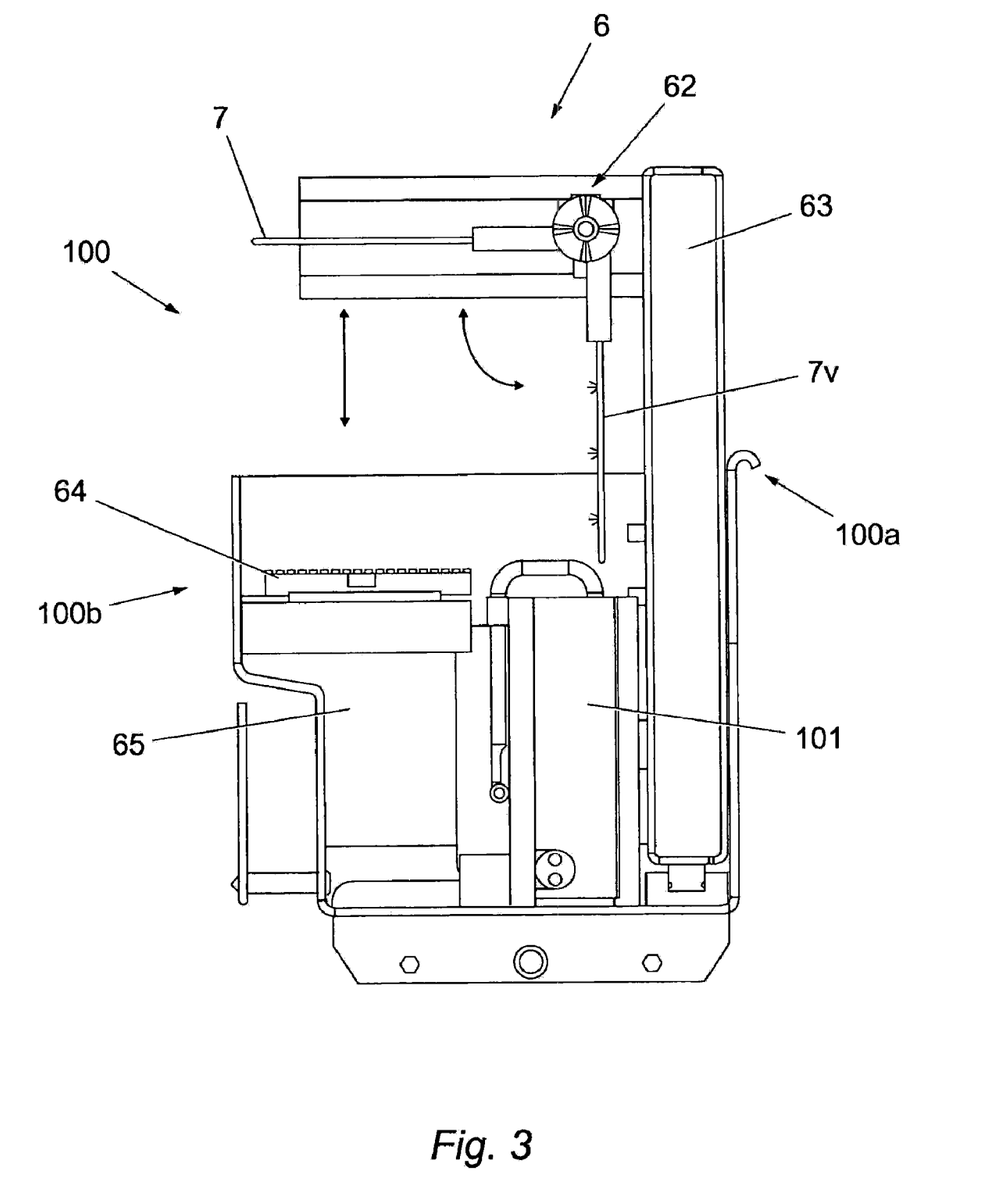
FIG. 3 is a schematic front view of a drawer assembly including a slide rack assembly and a dip tank in an apparatus according to the invention.

The slides 7 in the slide rack assembly 6 may be loaded and unloaded in a horizontal position when the slide rack assembly 6 may be in an upper position, as shown in FIG. 3. The slide rack assembly 6 may be arranged in a slide elevator 63 and the slide holder 62 may be adapted to pivot the slide 7 between a horizontal position to a vertical position 7v, when the slide rack 6 may be in an upper position. The slide rack assembly 6 may include a slide rack elevator 63 and may be arranged as a moving part 100a of a drawer assembly 100. In a corresponding stationary part 100b of the drawer assembly 100, a fluid containment element 101 or even a dip tank may be provided.

The system may include eight drawer assemblies, as shown in FIG. 1. However, it may be realized that any other number may also be provided depending on the design preferences. Each drawer assembly may include a drawer slide, a slide elevator 63, a slide rack assembly 6 which may include slide temperature control members 64, fluid containment element 101 or even a dip tank, a drip tray 65 for collecting staining fluids and a control means, or more broadly a control element which may include indicators for various user information and process surveillance purposes.

Figure 6:
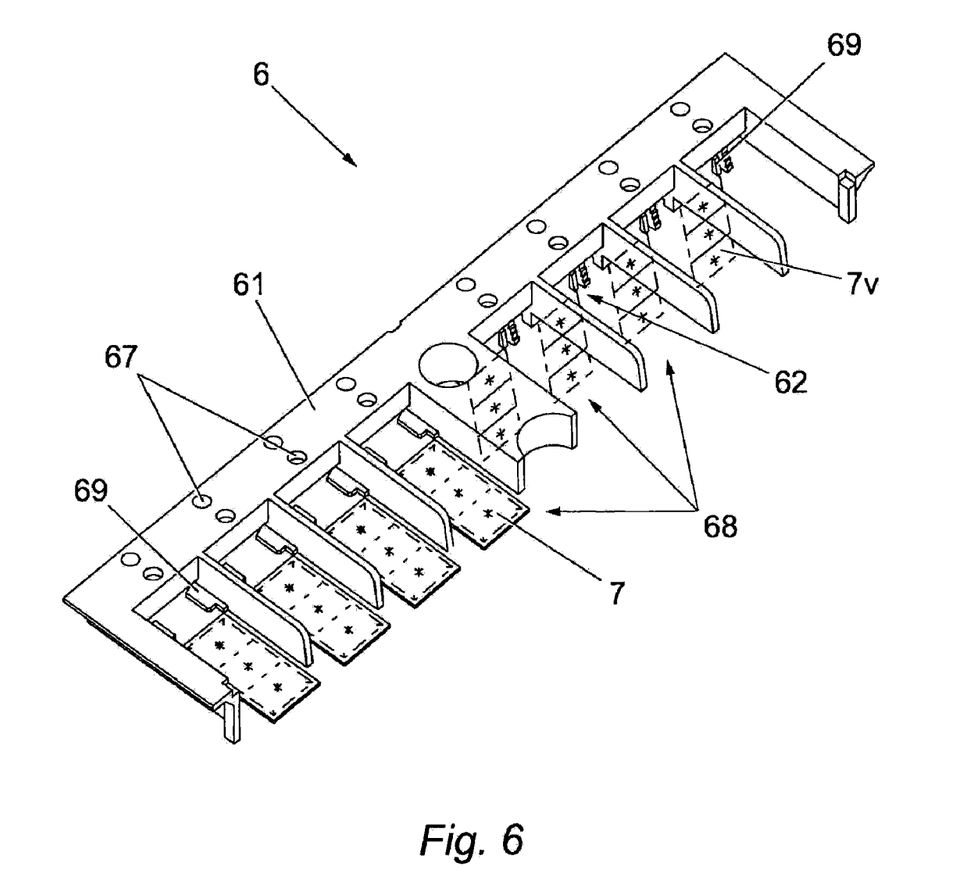
FIG. 6 is a perspective top view of a slide holder according to a preferred embodiment of the invention.

The slide rack assembly 6 may be shown in FIG. 6. The slide rack assembly 6 may include a slide rack 61 which may have a capacity of eight slides 7 in individual slide receiving compartments 68, as shown in FIG. 6. In connection with each compartment 68, a slide holder 62 may be provided. The slide holders 62 may include pivoting means or more broadly a vertical slide positioner which may include slide clips 69 and which may be pivotable between a horizontal slide position and a substantially vertical slide position and activation means 67. The slides 7, 7v may be individually pivotable in their slide holders 62, as the slide holder clips 69 may be pivoted by a pushing of a nesting tab 67, of which two are provided, one for pivoting from a horizontal to a vertical position and one for returning the slide from a vertical to a horizontal position.

Figure 4:
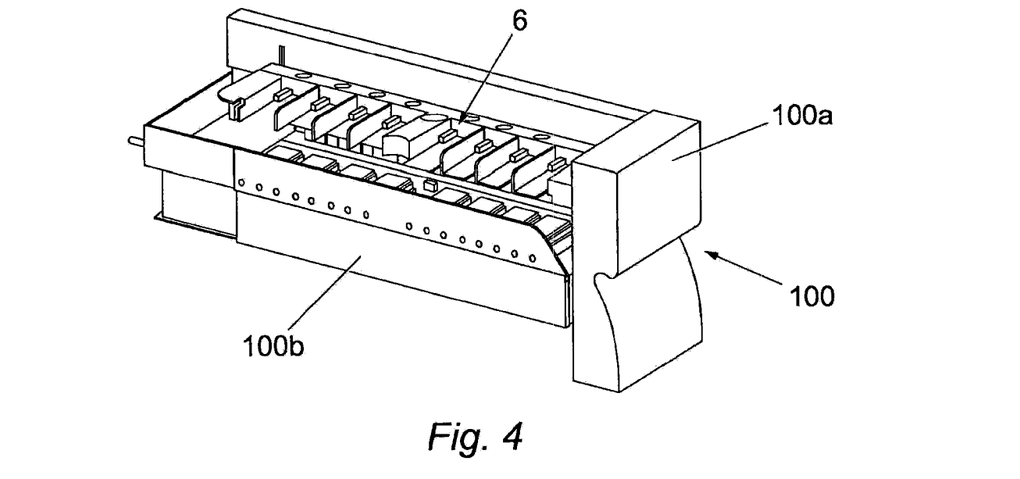
FIG. 4 is a perspective view of a drawer assembly in a closed position.
Figure 5:
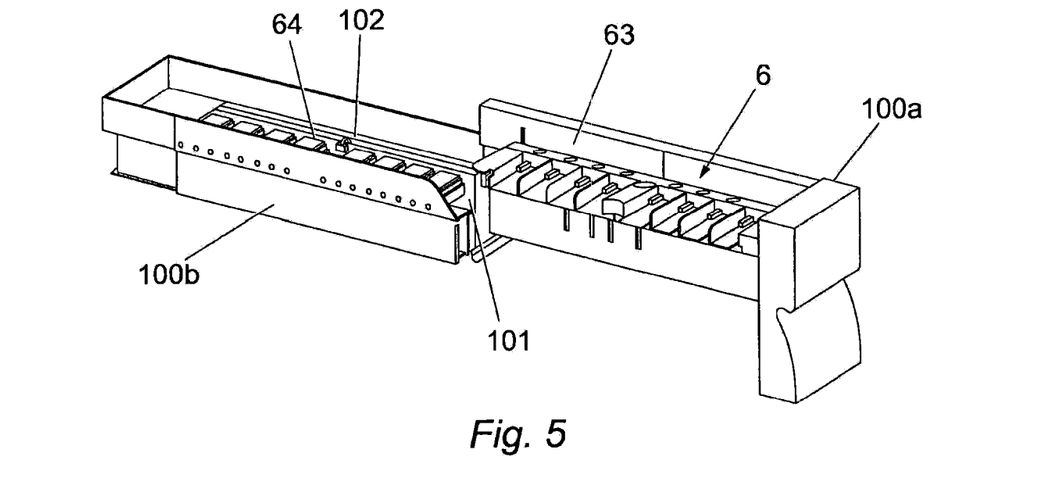
FIG. 5 is the drawer assembly of FIG. 4 in an open position.
Figure 7:
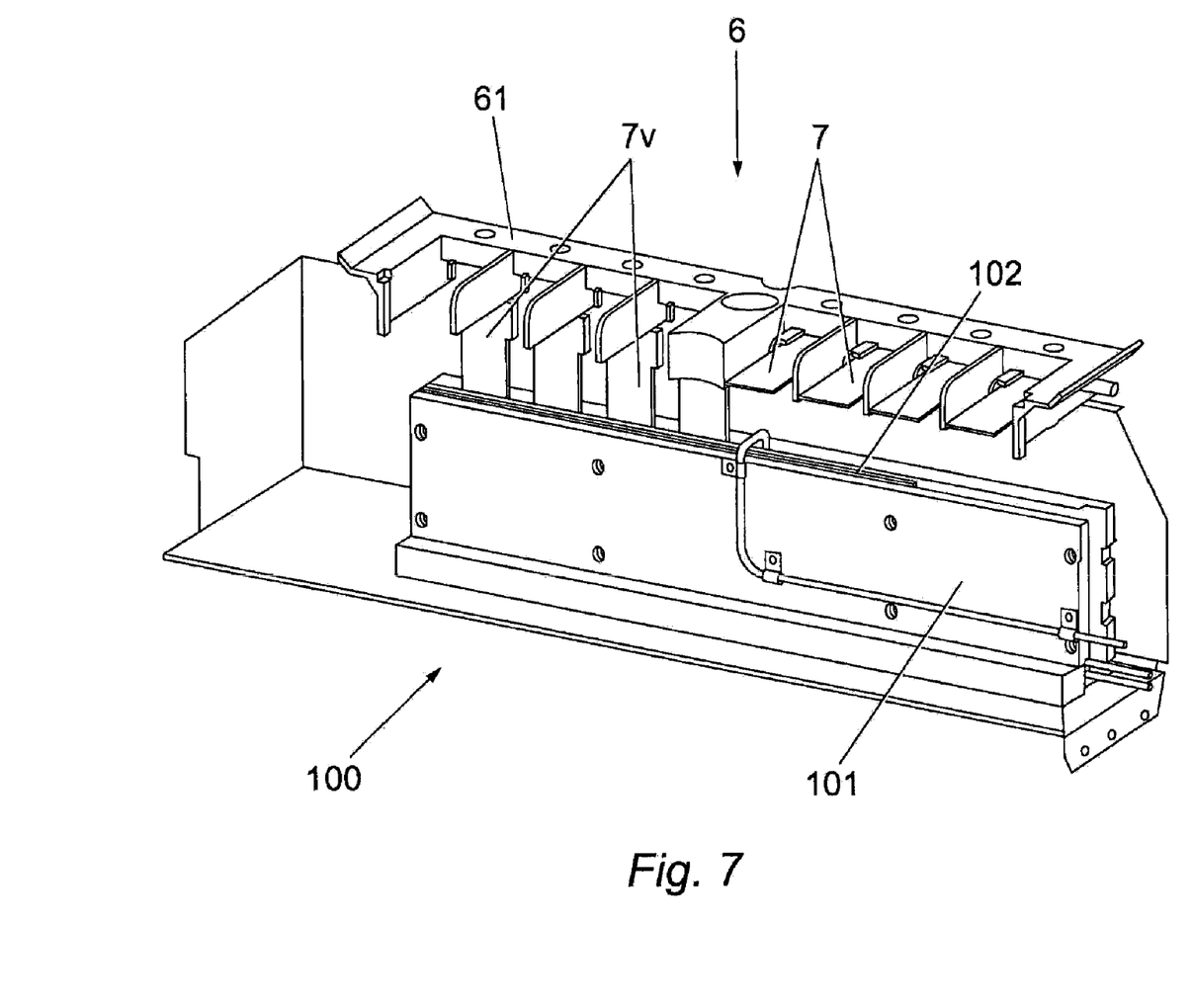
FIG. 7 is a detailed view of the slide holder and the dip tank arranged in a drawer assembly.

The slide rack may be in an upper position when the drawer 100 may be loaded with one or more slides 7 and also during the staining process. After the slides 7 have been loaded, the slides 7 may be pivoted to a vertical position 7v and then the slide rack 6 may be lowered by the slide elevator 63, such that the vertically disposed slides 7v may be immersed into an underlying fluid containment element 101 or even a dip tank. The drawer assembly may also be shown in the FIGS. 4, 5 and 7. The slide elevator 63 may be adapted to agitate the slides 7v while they are immersed in the dip tank fluid.

The dip tank may be filled with a predetermined amount of a processing fluid from a transfer tank (see FIG. 10) and may even be drained of fluid. The relevant processing fluid may have been prior to that transferred from a supply tank to the transfer tank via pneumatic pressure means. In embodiments, the present invention includes supplying a processing liquid from at least one supply tank in a dip tank. By using a transfer tank and controlling the fluid transfer by a pneumatic system including a vacuum pump, the pumping may be carried out without fluids coming into contact with pumping components. This may be advantageous since the risk of residues of fluids in the components may hereby be minimized.

A total of eight drawers may be provided. Accordingly, this may include that eight dip tanks may also be provided in the apparatus. Each fluid containment element 101 or even a dip tank may accommodate up to eight immersed slides 7v at the time. A primary function of the dip tank may be to heat the fluid in the tank up to a predetermined temperature, e.g. up to about 120° C. from ambient temperature in a certain amount of time, e.g. about 15 minutes and maintain the predetermined temperature, e.g. about 120° C. without any sign of boiling for a pretreatment processing time, e.g. about 10 to about 20 minutes after the slides have been lowered into the dip tank. After this process time may be passed, the heat may be turned off and the slides 7v may be removed by raising the slide rack assembly 6 and thereby lifting the vertical slides 7v out of the dip tank. In embodiments the present invention may include processing a tissue sample. The fluid containment element or even the dip tank may be used for deparaffinization, re-hydration, heat induced target retrieval, among other processes. A pretreatment process may include any process including but not limited to deparaffinization, re-hydration, heat induced target retrieval, and the like processes. These processes may be performed onboard the apparatus with the slides in a vertical orientation, immersed in individual tanks that can be filled with and emptied of various required reagents. For the target retrieval process, the fluid level in the dip tank may raise onto the label on the slide. The heating member may be adapted to heat up and maintain a temperature of approximately about 95° C. for a period of up to about 40 to about 60 minutes. The pretreatment process carried out in a fluid containment element or even the dip tank, may involve immersing the slides in a series of fluids for short periods of time, e.g. about 5 to about 10 minutes. The process of deparaffinization may be intended to first remove from the tissue sample the paraffin in which it may be mounted, then remove the paraffin solvent, and then through a series of reagents progressively re-hydrate the sample.

Figure 8:
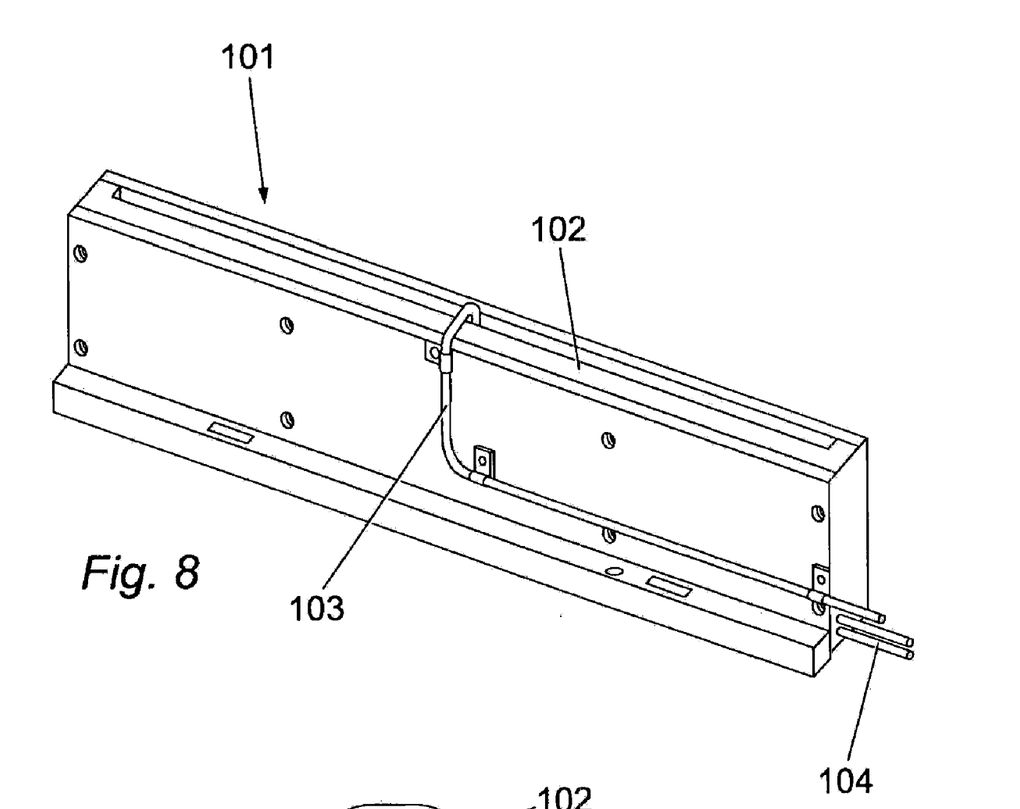
FIG. 8 is a perspective view of a dip tank according to the preferred embodiment of the invention.
Figure 9:
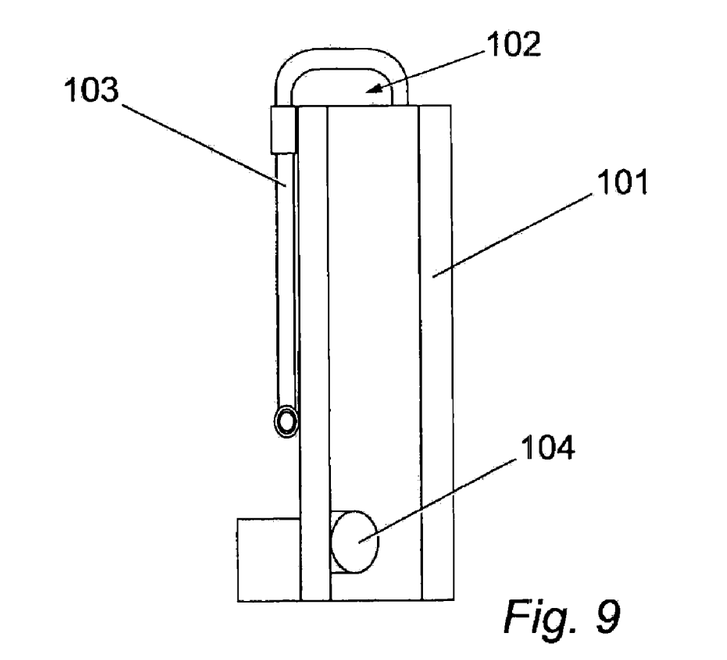
FIG. 9 is a front view of the dip tank of FIG. 8.

As shown in e.g. FIGS. 8 and 9, the fluid containment element 101 or even a dip tank may be elongated with an opening slot 102 through which the slides 7v may be inserted. This may result in a relative small dip tank volume, which in turn may allow for relatively rapid heating of the fluid in the tank and/or relatively low power consumption for heating up and maintaining the temperature of the fluid in the tank. The tank 101 may be filled and drained via a fluid connection tube 103 and the heating member 104 may be located in the lower section of the tank. The fluid containment element 101 or even a dip tank may be provided with insulating sidewall members on both sides to accelerate the heating thereby decreasing the heating times. The dip tank 101 may also be provided with sensor means (not shown) for registering the fluid level in the tank and a sensor for registering the temperature of the fluid, and feeding these data to the control system of the apparatus.

The pretreatment fluids or reagents may be stored in a number of individual containers, where some containers store fluids that are dedicated for deparaffinization, some for target retrieval and containers with 100% alcohol, distilled water and buffers. The containers may be advantageously provided with different volumes corresponding to the required amounts of the specific fluids for the performance of the pretreatment processes on the apparatus.

Figure 10:
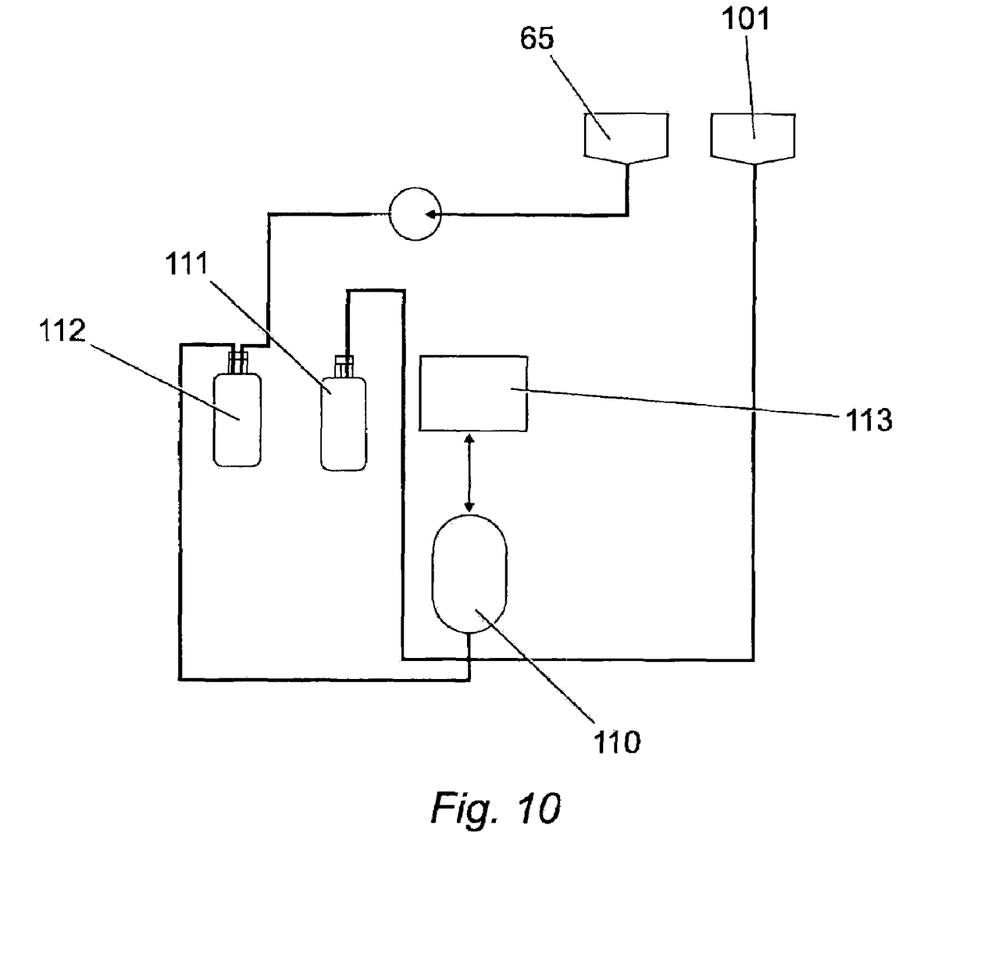
FIG. 10 is a fluidic diagram of the handling of processing liquid for the dip tank.

The fluid transfer between the supply containers 111 and the dip tanks 101 may be via a transfer tank 110, as shown in FIG. 10. In embodiments, the present invention may include a fluid transfer element configured to transfer fluid between a dip tank and a supply tank with a transfer tank. The fluid transfer may be accomplished through positive and negative air pressure applied to the transfer tank 110 which may even be accomplished by a pneumatic pressure control adapted to apply positive respective negative air pressure to a transfer tank. Two separate, dedicated transfer tanks (not shown) may be provided, one for aqueous solutions and a second for organic solutions. Similarly, for emptying the dip tanks, the waste fluid may be transferred via the transfer tank 110 to the waste containers 112. Dedicated waste tanks may be provided, e.g. one for hazardous waste fluids and one for non-hazardous waste fluids.

Fluids may be transferred in both directions between any container and any fluid containment element or dip tank. The operational sequence of the fluid transfers may be determined by the control system of the apparatus. The deparaffinization reagents may be reused and periodically cycled from clean to dirty. Used dirty deparaffinization fluids and dip tank rinse fluids may be discarded by the user or by the control system as hazardous waste. Target retrieval buffer and water are labelled "single use" fluids in the control system and transferred to waste after use.

Above, the apparatus and the method according to the invention are described according to some explanatory embodiments. However, it is realized by the invention that many other variations and equivalents of the method and the apparatus may be carried out without departing from the scope of the invention as specified in the accompanying claims.

As can be easily understood from the foregoing, the basic concepts of the present invention may be embodied in a variety of ways. It involves both tissue sample processing and staining techniques as well as devices to accomplish the appropriate processed and stained tissue samples. In this application, the tissue sample processing and staining techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used, the term "element" is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "slide immerser" should be understood to encompass disclosure of the act of "immersing"—whether explicitly discussed or not—and, conversely, were there effectively disclosure of the act of "immersing", such a disclosure should be understood to encompass disclosure of a "immerser" and even a "means for immersing" Such changes and alternative terms are to be understood to be explicitly included in the description.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of Information Disclosure Statement by Applicant or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the tissue sample processing and staining devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claims or concepts presented.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An automatic stainer system for staining at least one tissue sample, comprising:
   at least one slide comprising the at least one tissue sample;
   at least one reagent;
   at least one fluid containment element containing fluid for application to said at least one tissue sample;
   a slide rack comprising the at least one slide, said slide rack further including a slide positioner element adapted to pivot said at least one slide between at least a first disposition and a second disposition, wherein the first disposition is for submerging said at least one slide into said fluid in said fluid containment element and the second disposition is for application of said at least one reagent onto said at least one tissue sample;

a slide elevator for lowering said slide rack when said slide is pivoted to the first disposition, and submerging said at least one slide into said fluid containment element; and a reagent application element adapted to apply said at least one reagent to said at least one tissue sample during a staining operation performed on said at least one tissue sample when said at least one slide is pivoted to the second disposition.

2. The system according to claim 1, wherein said at least one reagent comprises at least two reagents arranged in a sequence according to a staining protocol.

3. The system according to claim 1, wherein said at least one fluid containment element applies the fluid to said at least one tissue sample during at least one pre-treatment operation performed prior to the staining operation.

4. The system according to claim 3, wherein said at least one pre-treatment operation comprises removal of an embedding medium from said at least one tissue sample.

5. The system according to claim 4, wherein the at least one pre-treatment operation is chosen from the group consisting of target retrieval and deparaffinization.

6. The system according to claim 5, wherein said at least one pre-treatment operation comprises both target retrieval and removal of an embedding medium from said at least one tissue sample.

7. The system according to claim 1, further comprising:

a drawer assembly adapted to retract from said system, wherein said drawer assembly comprises the slide rack.

8. The system according to claim 7, wherein said drawer assembly comprises a plurality of said drawer assemblies, each adapted to cooperate with said fluid containment element, at least one transfer tank, a supply tank, and at least one waste tank.

9. The system according to claim 1, wherein said fluid containment element comprises a heating member adapted to heat the fluid.

10. The system according to claim 1, wherein said fluid containment element comprises a dip tank.

11. The system according to claim 1, further comprising:

a pneumatic element adapted to transfer liquid from a supply tank to a transfer tank and from said transfer tank to said fluid containment element; and a drain element adapted to remove liquid from said fluid containment element to said transfer tank and from said transfer tank to a waste collection tank.

12. The system according to claim 1, wherein the first disposition is a substantially vertical disposition and the second disposition is a substantially horizontal disposition.

13. An automatic stainer system for staining at least one tissue sample, comprising:

at least one slide comprising the at least one tissue sample;

at least one reagent;

at least one fluid containment element containing fluid for application to said at least one tissue sample during at least one pre-treatment operation performed on said at least one tissue sample prior to a staining operation, wherein said at least one pre-treatment operation is chosen from the group consisting of target retrieval and deparaffinization;

a slide rack comprising the at least one slide, said slide rack further including a slide positioner element adapted to pivot said at least one slide between at least a first disposition and a second disposition, wherein the first disposition is for submerging said at least one slide into said fluid in said fluid containment element and the second disposition is for application of said at least one reagent onto said at least one tissue sample;

a slide elevator for lowering said slide rack when said slide is pivoted to the first disposition, and submerging said at least one slide into said fluid containment element; and a reagent application element adapted to apply said at least one reagent to said at least one tissue sample during a staining operation performed on said at least one tissue sample when said at least one slide is pivoted to the second disposition.

14. The system according to claim 13, wherein said at least one reagent comprises at least two reagents arranged in a sequence according to a staining protocol.

15. The system according to claim 13, further comprising:

a drawer assembly adapted to retract from said system, wherein said drawer assembly comprises the slide rack.

16. The system according to claim 15, wherein said drawer assembly comprises a plurality of said drawer assemblies, each adapted to cooperate with said fluid containment element, at least one transfer tank, a supply tank, and at least one waste tank.

17. The system according to claim 13, wherein said fluid containment element comprises a heating member adapted to heat the fluid.

18. The system according to claim 13, wherein said fluid containment element comprises a dip tank.

19. The system according to claim 13, further comprising:

a pneumatic element adapted to transfer liquid from a supply tank to a transfer tank and from said transfer tank to said fluid containment element; and a drain element adapted to remove liquid from said fluid containment element to said transfer tank and from said transfer tank to a waste collection tank.

20. The system according to claim 13, wherein the first disposition is a substantially vertical disposition and the second disposition is a substantially horizontal disposition.

\* \* \* \* \*